United States Patent [19]

Bressi, Jr.

[11] Patent Number: 5,443,479

[45] Date of Patent: Aug. 22, 1995

[54] SURGICAL FORCEPS

[76] Inventor: Thomas E. Bressi, Jr., 909 Waverly Rd., Bryn Mawr, Pa. 19010

[21] Appl. No.: 193,400

[22] Filed: Feb. 7, 1994

[51] Int. Cl.⁶ ............................................. A61B 17/28
[52] U.S. Cl. ..................................... 606/205; 606/208
[58] Field of Search ................. 606/51, 52, 83, 170, 606/174, 205–211; 128/750–755; 81/418, 420, 419, 424

[56] References Cited

U.S. PATENT DOCUMENTS

| 4,763,665 | 8/1988 | Jaeger | 128/751 |
| 4,880,015 | 11/1989 | Nierman | 128/751 |
| 5,209,747 | 5/1993 | Knoepfler | 606/208 |

*Primary Examiner*—Stephen C. Pellegrino
*Assistant Examiner*—William Lewis
*Attorney, Agent, or Firm*—Norman E. Lehrer; Jeffrey S. Ginsberg

[57] ABSTRACT

A surgical forceps of the type that has a handle, an elongated tube mounted to the handle, and a pair of jaw members connected to the handle through the elongated tube so that manipulation of the handle will open and close the jaw members. The jaw members of the present invention have a large curved segment, a reduced curved segment and a slot positioned between the large curved segment and the reduced curved segment. The large curved segments form in association with one another a first rounded, oval or circular shape and the reduced curved segments form in association with one another a second rounded, oval or circular shape. The jaw members can be deflected about the elongated tube.

8 Claims, 3 Drawing Sheets

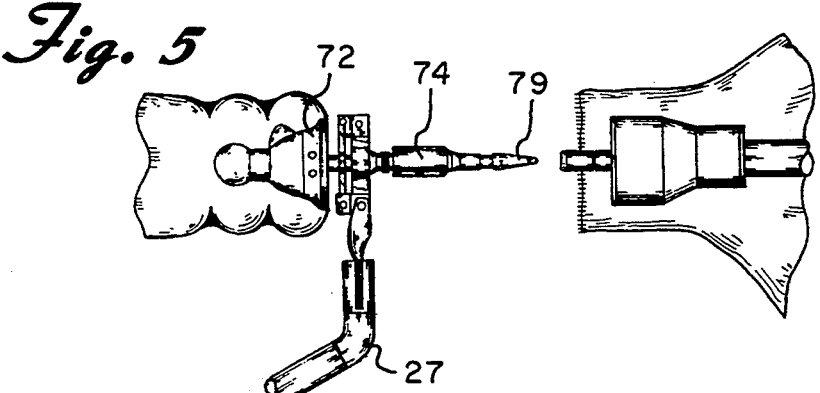
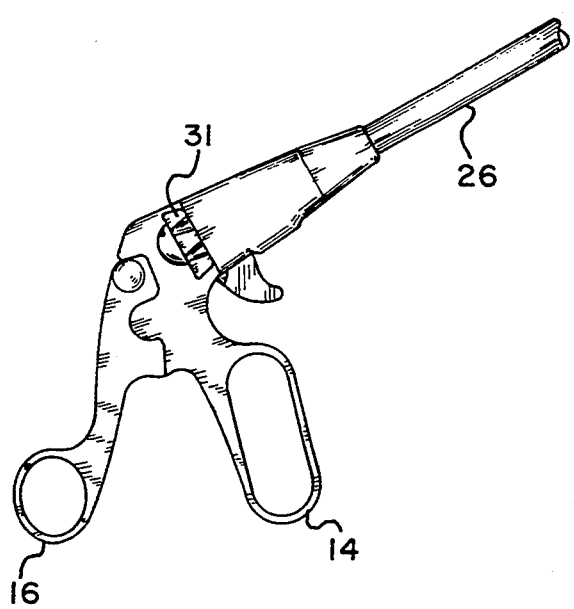
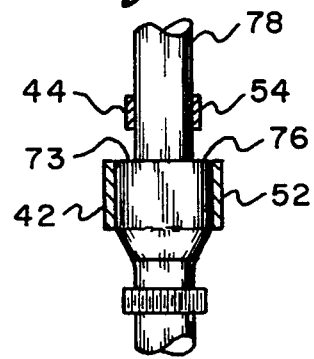
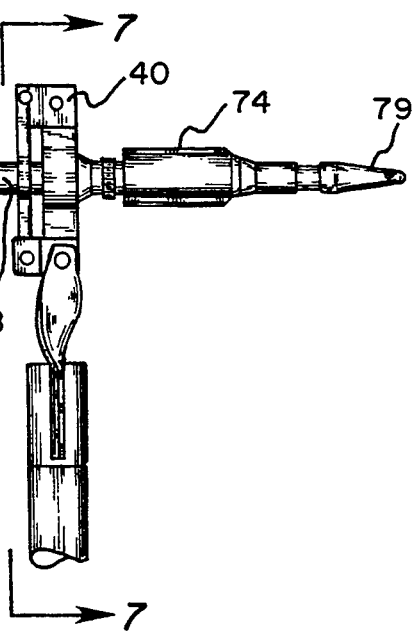
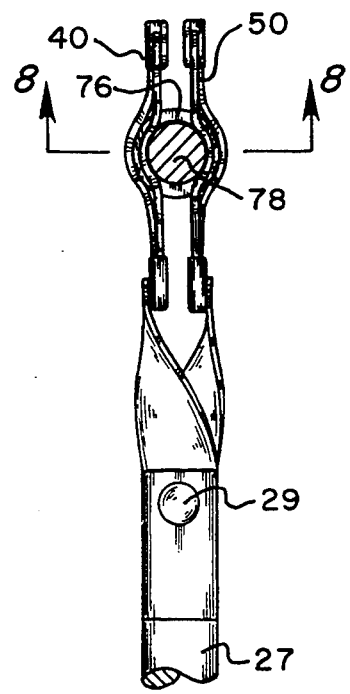

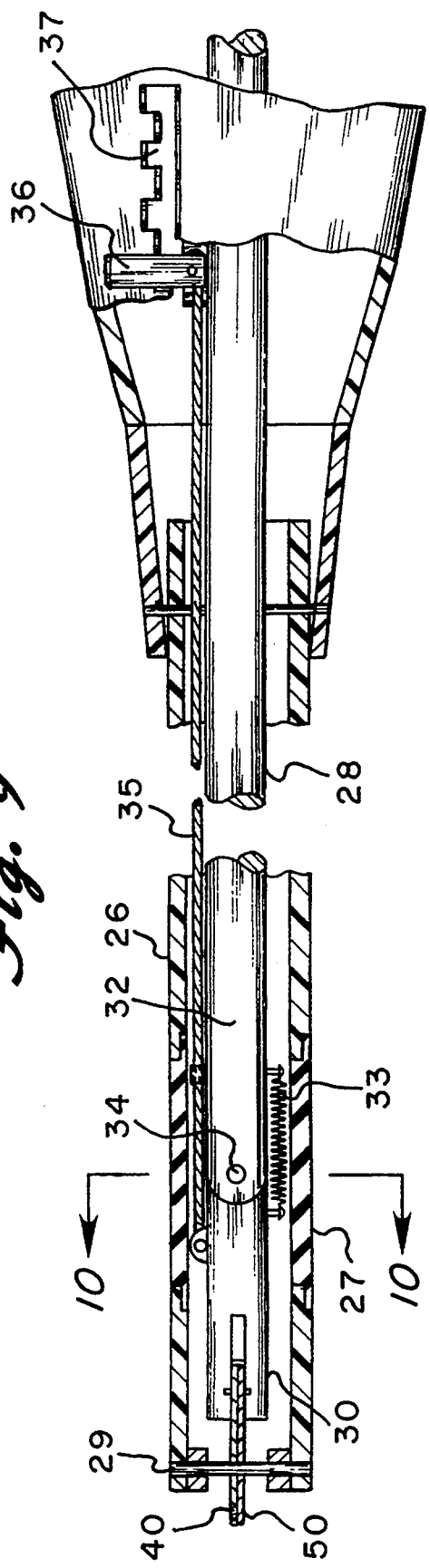
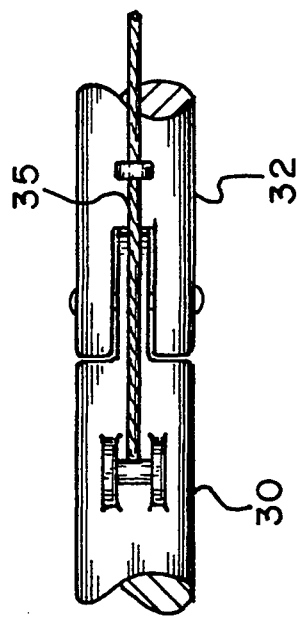
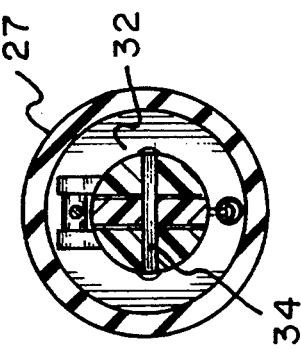

SURGICAL FORCEPS

BACKGROUND OF THE INVENTION

The present invention relates to surgical forceps for firmly grasping a shaft that has a large diameter segment and a reduced diameter segment and, more particularly, to such forceps including a pair of jaw members, each having a large curved segment, a reduced curved segment and a slot positioned between the large and reduced curved segments. Additionally, the invention relates to surgical forceps having jaw members that are capable of bending so that the forceps can be properly manipulated during a laparoscopic procedure.

Forceps used in surgical procedures must be able to firmly grasp the medical device that is being inserted into and removed from the human body in order to prevent the medical device from slipping inside the patient. This is to ensure that the surgical procedure can be carried out both safely and accurately.

Most existing surgical forceps are not adapted to properly grasp medical instruments that have shafts with differing diameters. Such forceps are shown, for example, in prior U.S. Pat. Nos. 2,113,246, 2,397,823, 3,316,913, 3,585,985, 3,636,954, 4,088,134, 4,165,746, 4,286,598, 4,462,404 and 4,484,911. Moreover, the aforementioned patents do not disclose jaw members that are bendable to allow the surgeon to reach places that are difficult to navigate.

In U.S. Pat. 4,950,275 pincers for grasping a bowel anastomosis ring holder are disclosed. The pincers have a pair of jaws, each of which has an upper claw and a lower claw. Although, the upper and lower claws each form an oval or circular shape when the pincers are in the closed condition, only the lower claws grasp the bowel anastomosis ring.

Accordingly, there is a need for an improved surgical forceps that can firmly grasp a shaft that has two different diameters and provides the user with access to hard to reach areas.

SUMMARY OF THE INVENTION

The present invention is designed to overcome the deficiencies of the prior art discussed above. It is an object of this invention to provide surgical forceps that can firmly grasp a shaft that has a large diameter segment and a reduced diameter segment.

It is a further object of this invention to provide surgical forceps that have deflectable jaw members.

In accordance with the illustrative embodiments, demonstrating features and advantages of the present invention, there is provided an improved surgical forceps of the type having A pair of jaw members connected to a handle through an elongated tube. The improvement lies in the jaw members. In the present invention, the jaw members each have a large curved segment, a reduced curved segment and a slot positioned between the large and reduced curved segments. The large curved segments form, in association with one another, a first oval or circular shape and the reduced curved segments, form in association with one another, a second oval or circular shape.

The present invention makes it possible to firmly grasp a shaft that has a large diameter segment and a reduced diameter segment and tightly hold onto it, so that there is no transverse slippage of the shaft relative to the jaw members. In the preferred embodiment, the present invention is used in conjunction with a surgical stapler used during a laparoscopic bowel anastomosis. The surgical stapler includes a detachable anvil that has a spindle with a large diameter segment and a reduced diameter segment. The present invention allows the surgeon to firmly grasp the spindle portion with the forceps during the anastomosis procedure. Thus, the surgeon can exert strong counter pressure without the anvil slipping and becoming dislodged in the proximal colon.

In the preferred embodiment, the forceps include means for bending the jaw members. This is desirable when the surgical forceps are partially inserted into a human body, i.e. during a laparoscopic procedure, as the surgeon must be able to maneuver the forceps in areas that are difficult to navigate.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 5 is a view showing the jaw members of the present invention firmly grasping the spindle portion of a detachable anvil of a surgical stapler, FIG. 6 is a top view showing the jaw members of the present invention firmly grasping the spindle portion of a detachable anvil of a surgical stapler, FIG. 7 is a cross-sectional view taken through the line 7—7 of FIG. 6, FIG. 8 is a partial cross-sectional view taken through the line 8—8 of FIG. 7, FIG. 9 is a partial cross-sectional view of the forceps, FIG. 10 is a partial cross-sectional view taken through line 10—10 of FIG. 9, and FIG. 11 is a partial view of the rod and attached bending cable.

DETAILED DESCRIPTION OF THE PREFERRED EMBODIMENTS

Figure 1:
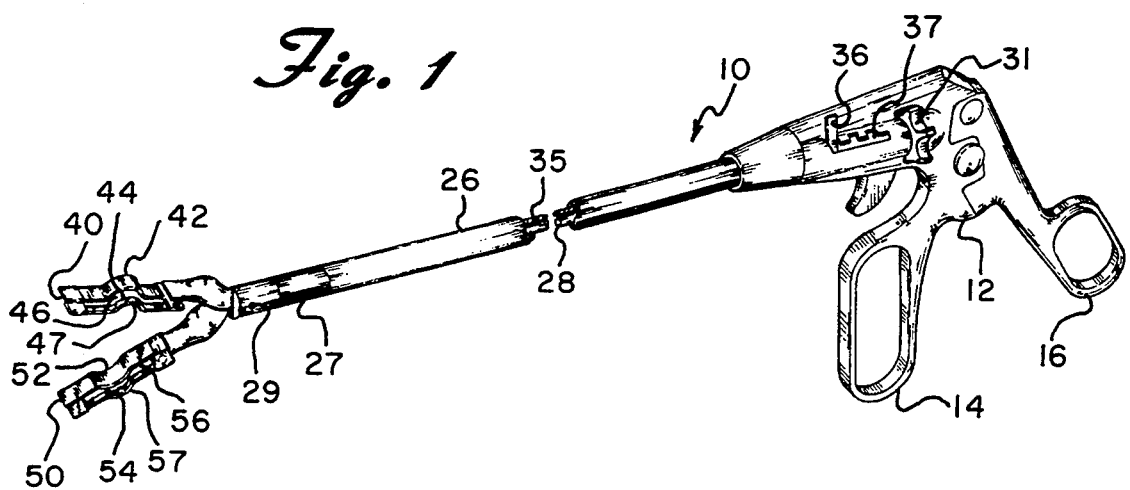
FIG. 1 is a front perspective view, partially in section, of a surgical forceps constructed in accordance with the principles of the present invention.

Referring now to the drawings in detail wherein like reference numerals have been used throughout the various figures to designate like elements, there is shown in the figures surgical forceps constructed in accordance with the principles of the present invention and designated generally as 10.

As with other similar surgical forceps, the present invention includes a handle 12 having a finger receiving segment 14 movably connected to a thumb receiving segment 16 against the action of an elastic restoring force (see FIG. 1). An elongated tube 26 extends from the handle 12. The elongated tube 26 has a disc 31 attached to one end. The disc 31 is rotatably mounted in the handle 12 so that rotation of the disc 31 rotates the attached elongated tube 26. A rod 28 located within elongated tube 26 is connected to handle 12. First jaw member 40 and second jaw member 50 are partially inserted in elongated tube 26 and rod 28. A pin 29 connects jaw members 40 and 50 to the elongated tube 26 through a common point of intersection. The jaw members 40 and 50 are connected to the rod 28 in a known manner so that when the handle 12 is manually manipulated, the rod 28 is drawn toward the handle 12 thereby causing the jaw members 40 and 50 to converge.

Figure 2:
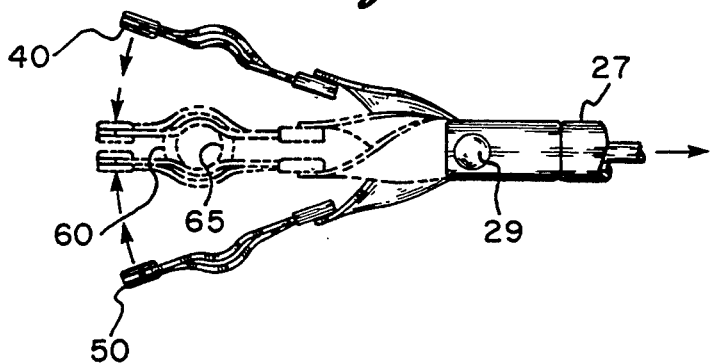
FIG. 2 is a partial side view of the jaw members of the surgical forceps showing the jaw members in both the open and closed positions.
Figure 3:
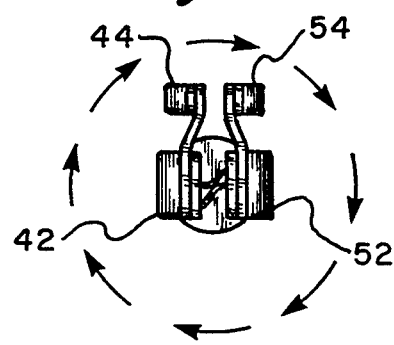
FIG. 3 is a frontal view of the jaw members of the surgical forceps showing rotation about the handle.

In the present invention, the first jaw member 40 has a large curved or rounded segment 42, a reduced curved or rounded segment 44 and a slot 46 positioned between the large curved segment 42 and the reduced curved segment 44 (see FIGS. 1–2). The slot 46 defines an inside shoulder 47 on the reduced curved segment 44. Similarly, the second jaw member 50 has a large curved or rounded segment 52, a reduced curved or rounded segment 54 and a slot 56 positioned between the large curved segment 52 and the reduced curved segment 54. The slot 56 defines an inside shoulder 57 on reduced curved segment 54. When the handle 12 is manually manipulated, the jaw members 40 and 50 converge (see FIG. 2). The large curved segments 42 and 52 form in association with one another a first, oval or circular shape 60 and the reduced curved segments 44 and 54 form in association with one another a second, oval or circular shape 65 (see FIG. 2).

The forceps of the present invention can firmly grasp and tightly hold onto a shaft that has a large diameter segment and a reduced diameter segment. In the preferred embodiment, the forceps are used in conjunction with a surgical stapler (shown in part in FIGS. 5 and 6) during a bowel anastomosis procedure. The surgical stapler has an anvil 72 detachably connected to a spindle 74. The spindle 74 has a large diameter segment 76, a reduced diameter segment 78 and a pointed tip 79 (see FIGS. 6 and 8). The diameter of the first shape 60 is approximately equivalent to the large diameter segment 76 of the spindle 74. Similarly, the diameter of the second shape 65 is approximately equivalent to the reduced diameter segment 78 of the spindle 74.

Figure 4:
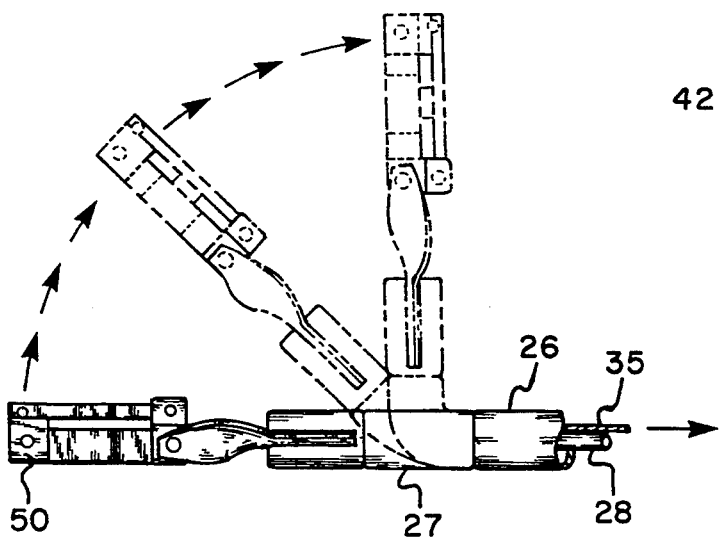
FIG. 4 is a top view of an embodiment that shows bendable jaw members.

In the preferred embodiment, the rod 28 includes a first segment 30 and a second segment 32 pivotally connected to each other at bending pivot point 34 (see FIG. 9). One end of a bending cable 35 is connected to the first segment 30. A locking element 36 slidably mounted in the handle 12 connects the other end of the bending cable 35 to the handle. When the locking element is manually manipulated, the bending cable 35 causes the first segment 30 of the rod 28 to deflect from the second segment 32 until a predetermined angle of deflection is achieved (see FIG. 4). The locking element 36 can be secured in one of a plurality of notches 37 to maintain the desired angle of deflection.

The elongated tube 26 includes a section 27 around the pivot point 34 that is made of a flexible material so that it bends when first segment 30 is deflected. Additionally, the elongated tube 26 is preferably smooth with a substantially continuous diameter of less than 0.5". Spring 33 is connected to the first and second segments 30 and 32 of the rod 28 so that an elastic restoring force is created when the first segment 30 is deflected from the second segment 32.

To facilitate an understanding of the principles associated with the foregoing apparatus, its operation will now be briefly described. During an anastomosis procedure, an anvil 72 and attached spindle 74 are inserted into the proximal colon. The jaw members 40 and 50 are positioned around spindle 74. The large curved segments 42 and 52, of jaw members 40 and 50, simultaneously grasp the large diameter segment 76 of spindle 74 and the reduced curved segments 44 and 54 simultaneously grasp the reduced diameter segment 78 when the thumb receiving segment 16 is manually manipulated to approach the finger receiving segment 14 of the handle 12.

The inside shoulders 47 and 57 engage step 73, so that there is no transverse slippage of the spindle 74 relative to jaw members 40 and 50 (see FIG. 8). The surgeon can then direct the spindle 74 and attached anvil 72 into the surgical stapler located in the rectal stump. Since the surgeon is able to firmly grasp the spindle, the risk of internal injury to the patient or loss of the spindle is reduced.

During a laparoscopic anastomosis procedure, the jaw members 40 and 50 must be able to deflect so that the surgeon can properly maneuver the forceps. This is accomplished by manually manipulating the locking element 36 so that the bending cable 35 moves towards the handle 12, thereby causing the first segment 30 of rod 28 to deflect from the second segment 32 about the bending pivot point 34. Since section 27 of the elongated tube 26 is made of a flexible material it does not substantially hinder the deflection. When a desired degree of deflection has been obtained, the locking element 36 is secured in the appropriate notch 37 located in the handle 12.

The present invention may be embodied in other specific forms without departing from the spirit or essential attributes thereof and accordingly reference should be made to the appended claims rather than to the foregoing specification as indicating the scope of the invention.

I claim:

1. In a surgical forceps of the type having a handle, an elongated tube mounted to said handle, first and second jaw members, and means for attaching said jaw members to said handle so that manipulation of said handle will open and close said jaw members, wherein the improvement comprises each of said jaw members having a large curved segment, a reduced curved segment and a slot positioned between said large curved segment and said reduced curved segment, said large curved segments of said jaw members form in association with one another a first rounded shape and said reduced curved segments of said jaw members form in association with one another a second rounded shape, said slot defining an inside shoulder on said reduced diameter segment.

2. The forceps of claim 1, wherein said elongated tube extends from said handle, said tube having one end rotatably mounted in said handle.

3. In a surgical forceps of the type having a handle, an elongated tube mounted to said handle, first and second jaw members, and a rod for attaching said jaw members to said handle so that manipulation of said handle will open and close said jaw members, wherein the improvement comprises means for deflecting said rod about a bending pivot point so that a predetermined angle of deflection can be achieved, said rod having a first segment and a second segment, said first segment and said second segment being pivotally connected to one another at said bending pivot point and being located within said elongated tube, said first segment being connected to said first and second jaw members, said second segment being connected to said handle, said means for deflecting said first and second segments of said rod including a locking element slidably mounted in said handle, and a bending cable having a first end and a second end, said first end being connected to said first segment of said rod and said second end being connected to said locking element so that manual manipulation of said locking element causes said first segment to deflect from said second segment as said bending cable is drawn toward said handle, said elongated tube having a portion made of flexible material, said forceps further including means for creating an elastic restoring force when said first segment is deflected from said second segment.

4. The forceps of claim 3, wherein each of said jaw members has a large curved segment, a reduced curved segment and a slot positioned between said large curved segment and said reduced curved segment, said large curved segments of said jaw members form in association with one another a first rounded shape and said reduced curved segments of said jaw members form in association with one another a second rounded shape, said slot defining an inside shoulder on said reduced diameter segment.

5. In a surgical forceps of the type having a handle, an elongated tube mounted to said handle, first and second jaw members, and a rod for attaching said jaw members to said handle so that manipulation of said handle will open and close said jaw members, wherein the improvement comprises said rod having first and second segments, said first segment being connected to said first and second jaw members, said second segment being connected to said handle, said first and second segments being pivotally connected to one another at a bending pivot point so that a predetermined angle of deflection can be achieved, and said rod being entirely located within said elongated tube.

6. The forceps of claim 5, wherein the means for deflecting said first and second segments of said rod includes a locking element slidably mounted in said handle, and a bending cable having a first end and a second end, said first end being connected to said first segment of said rod and said second end being connected to said locking element so that manual manipulation of said locking element causes said first segment to deflect from said second segment as said bending cable is drawn toward said handle.

7. The forceps of claim 6 wherein at least a portion of said elongated tube is made of flexible material.

8. The forceps of claim 7 further including a spring connected to said first and second segments of said hollow rod so that an elastic restoring force is created when said first segment is deflected from said second segment.

* * * * *